(12) United States Patent
Kargenian

(10) Patent No.: US 7,991,490 B2
(45) Date of Patent: Aug. 2, 2011

(54) CONTROL UNIT FOR UTILITY TREATMENT SYSTEMS

(75) Inventor: John H. Kargenian, Buffalo Grove, IL (US)

(73) Assignee: Aquion, Inc., Elk Grove Village, IL (US)

( * ) Notice: Subject to any disclaimer, the term of this patent is extended or adjusted under 35 U.S.C. 154(b) by 622 days.

(21) Appl. No.: 11/295,423

(22) Filed: Dec. 5, 2005

(65) Prior Publication Data

US 2007/0129825 A1    Jun. 7, 2007

(51) Int. Cl.
*G05B 15/00* (2006.01)
(52) U.S. Cl. ............................................ 700/83; 700/17
(58) Field of Classification Search .................. 700/17, 700/18, 32, 83; 210/85, 87, 138, 232, 294
See application file for complete search history.

(56) References Cited

U.S. PATENT DOCUMENTS

| | | | | |
|---|---|---|---|---|
| 5,180,491 A * | 1/1993 | Polasky | | 210/282 |
| 5,443,734 A * | 8/1995 | Fetner et al. | | 210/656 |
| 5,494,573 A * | 2/1996 | Schoenmeyr et al. | | 210/94 |
| 5,583,058 A * | 12/1996 | Utsumi et al. | | 250/338.4 |
| 5,694,926 A * | 12/1997 | DeVries et al. | | 73/861.02 |
| 5,779,911 A * | 7/1998 | Haug et al. | | 210/739 |
| 6,312,589 B1 * | 11/2001 | Jarocki et al. | | 210/87 |
| 6,753,186 B2 * | 6/2004 | Moskoff | | 210/94 |
| 6,772,095 B2 * | 8/2004 | Sakamoto et al. | | 702/184 |
| 6,826,267 B2 * | 11/2004 | Daum et al. | | 379/102.03 |
| 6,975,968 B2 * | 12/2005 | Nakamitsu et al. | | 702/184 |
| 7,008,529 B2 * | 3/2006 | Nakanishi et al. | | 210/98 |
| 7,409,301 B2 * | 8/2008 | Tynkov | | 702/55 |
| 7,638,042 B2 * | 12/2009 | Astle et al. | | 210/85 |
| 7,670,485 B2 * | 3/2010 | Duplessis et al. | | 210/190 |
| 2002/0062221 A1 * | 5/2002 | Seibert | | 705/1 |
| 2004/0181349 A1 * | 9/2004 | Tynkov | | 702/55 |
| 2007/0119758 A1 * | 5/2007 | Duplessis et al. | | 210/85 |
| 2007/0119768 A1 * | 5/2007 | Duplessis et al. | | 210/294 |

* cited by examiner

*Primary Examiner* — Charles R Kasenge
(74) *Attorney, Agent, or Firm* — Vedder Price P.C.

(57) ABSTRACT

A system and method for control and maintenance units for utility treatment systems, having a start-up routine, an installation routine and a communication exchange between a user and the control unit of a utility treatment system. Communications from the control unit prompt the user for installation and maintenance information; communications from the user supply installation, set-ups, status, operation and maintenance information. The communication exchange allows a user to contact the system and request information regarding a particular treatment system and the system to display treatment system information. The system and method also include a control unit for a utility treatment system having an electronic controller, an input device connected to the controller, and a storage device connected to the controller, wherein historical repair codes may be inputted to the electronic controller and stored in said storage device.

11 Claims, 2 Drawing Sheets

CONTROL UNIT FOR UTILITY TREATMENT SYSTEMS

FIELD OF THE INVENTION

The present invention relates generally to a electronic control unit for associated air, water and/or other utility treatment systems. The control unit controls the flow, monitors the flow, and controls the recordation and dissemination of operation and maintenance information from various treatment systems by providing an effective interface for the exchange of data between treatment systems and their users (e.g., owners, manufacturers, installers and service providers).

BACKGROUND OF THE INVENTION

The invention relates generally to utility treatment control systems, and more particularly, control systems for operating, monitoring and recording information for water, air, and/or other utility filtration, conditioning and/or treatment systems (hereinafter "treatment systems"). Treatment systems depend on the use of sensors, timers, inputs and outputs for control and monitoring, including remote display and operation. Of course, in order to function at peak effectiveness, treatment systems require very specific and timely monitoring and maintenance. Because treatment systems are made by different manufacturers without the ability to function through a central control system, they often must be installed independent of each other. This results in a lack of uniformity between the various control units with respect to available system data, alarm notifications, monitoring capability, remote access, and maintenance procedures, among other things. These variants reduce efficiency and increase the operating cost of treatment systems.

For example, water softening systems of the ion exchange type often include a tank having a bed of ion exchange resin. The resin material is usually non-soluble and effectively acts as a permanent anion to which exchangeable cations can attach. During the softening process, the hardness-causing ions in the water are exchanged with the "soft" sodium ions of the resin bed, thus producing softened water. After prolonged contact of the resin bed with hard water, however, the ion exchange capacity of the resin bed diminishes, and regeneration of the resin bed must be performed.

Regeneration of the resin bed is normally performed in distinct steps during what is called the regeneration cycle. First, the bed is cleansed during a backwash cycle, where the normal water flow across the resin bed is reversed to expand the resin bed and remove any deposits that may be trapped in the resin bed. Second, a brine solution (i.e., an aqueous solution of sodium chloride or the like) from a separate brine tank is introduced to the resin bed. When the brine contacts the resin bed, the aforementioned ion exchange process is reversed, i.e., the "hard" ions in the resin bed are replaced with "soft" ions from the brine solution. Thereafter, a rinse cycle is normally provided to wash the brine from the resin bed. Lastly, the brine tank is refilled to form brine for the next regeneration cycle. Due to the particular demands placed upon the water softening system, it is often desirable for a user to vary the length of time for each individual regeneration cycle to adjust for various tank sizes and volumes of resin. Regeneration, in general, can be performed on a set schedule, but is preferably performed based on the actual usage of the water softening system. The latter type of regeneration, known as "demand initiated regeneration", is generally regarded as a more efficient process.

Similar to the regeneration cycle used in water softening systems, treatment systems generally run through routine cycles that require system monitoring, data recordation and maintenance for varying time periods. When treatment systems are installed individually using discrete controllers (manual or electronic) for each system, the data critical to proper operation and maintenance of these systems can get lost in the shuffle. For example, manually controlled systems generally do not provide a recordation system for baseline or cycle related data. Without this information, routine maintenance is difficult to track and system malfunctions are more complicated and expensive to repair.

Although computerized controllers are better able to record system information to assist repair and service calls, the prior art controllers are system specific are limited in their ability to provide for accurate data input and output, among other things. Accordingly, there is a need for an improved control unit for utility treatment systems. In one embodiment of the present invention, installation, maintenance and operations information for one or more utility treatment systems is inputted or reviewed by a user through use of a sophisticated menu hierarchy and then stored in the control unit memory, which is accessible to all users. As used herein, the term "user" can include any person or entity that may be accessing, programming, maintaining, installing or in any way interacting with the control unit (e.g., the owner, service provider, manufacturer, installer). A user is able to access the stored installation, maintenance, and operations data archives either on site at the control unit or remotely by electronic means (e.g., modem and computer), allowing the user to supervise and properly respond to any system malfunction or maintenance/service issue in a timely and cost effective manner.

There is also a need for a two-step installation procedure, where an initial electrical test is performed and after completion of that electrical test, important baseline data is entered and saved to the control unit A two-step installation procedure according to one embodiment of the present invention facilitates the entry and recordation of baseline data that affects treatment system operations, maintenance and repairs. Such information can be available for reference when needed. The user is then able to further customize and operate the treatment system without fear of losing any system critical or otherwise notable historical system information.

These and other needs will become apparent upon a further reading of the following detailed description taken in conjunction with the drawings.

SUMMARY

One embodiment includes a system and method for control and maintenance units for utility treatment systems, having at least one start-up routine, at least one installation routine and a communication exchange between a user and the control unit of a utility treatment system. Communications from the control unit prompt the user for installation and maintenance information; communications from the user supply installation, set-up, status, operation and maintenance information. The communication exchange allows a user to contact the system and request information regarding a particular treatment system and the system to display treatment system information. Preferably, the system and method for control and maintenance units for utility treatment systems enables efficient communication exchange through an organized menu hierarchy, enabling a participating user to more effectively monitor and maintain utility treatment systems. Another embodiment includes a control unit for a utility treatment system having an electronic controller, an input device connected to the controller, and a storage device connected to the controller, wherein historical repair codes may be inputted to the electronic controller and stored in said storage device.

DESCRIPTION OF THE PREFERRED EMBODIMENT

Figure 1:
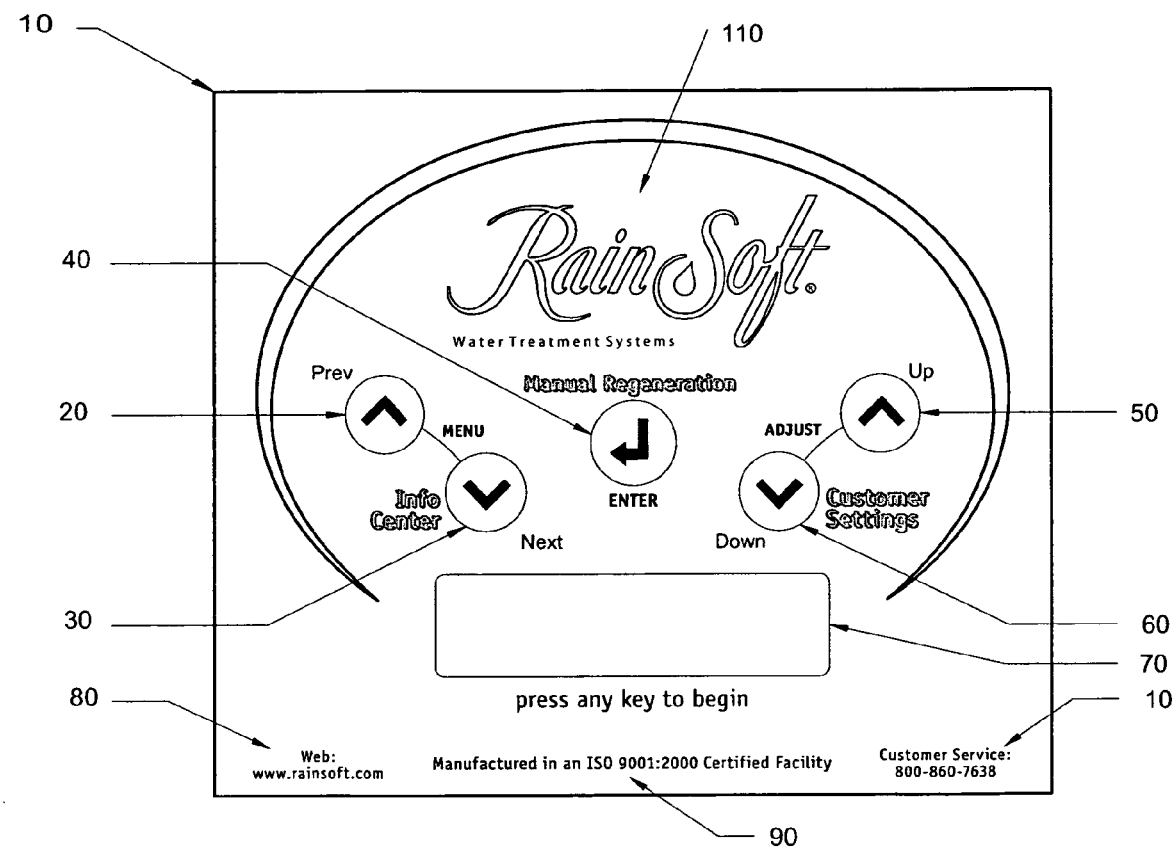
FIG. 1 is a front view of a control unit for a water treatment system according to one embodiment of the present invention.

While the present invention is capable of embodiment in various forms, there is shown in the drawings and described herein will hereinafter be described as a preferred embodiment with the understanding that the present disclosure is to be considered an exemplification of the invention, and is not intended to limit the invention to the specific embodiments illustrated.

Figure 2:
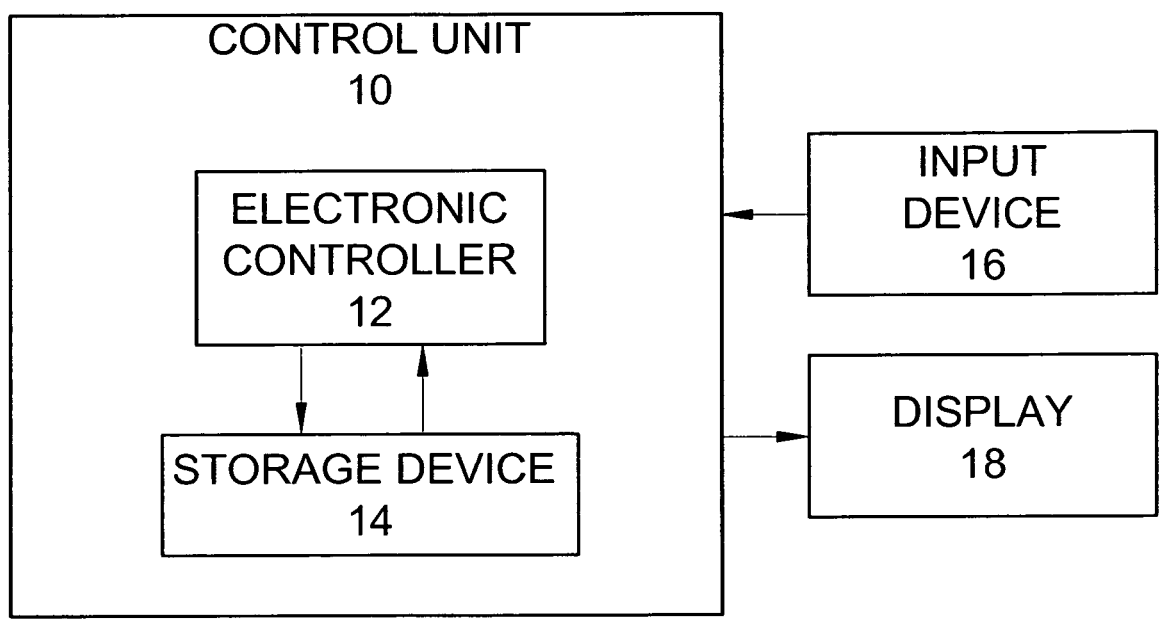
FIG. 2 is a diagram of a control unit for utility treatment systems according to one embodiment of the present invention.

One embodiment of the present invention provides a customizable and interactive electronic control unit which provides for the recordation and communication of installation, operation, maintenance and repair data for numerous treatment systems. For the purpose of illustration and not limitation, a control unit 10 of one preferred embodiment of the present invention is shown in FIGS. 1 and 2. The control unit 10 includes and input device 16 with two scroll keys 20, 30, an enter key 40, two adjustment keys 50, 60, a display screen 70 (backlight when the control unit is active), manufacturer website information 80, manufacturer facility information 90, customer service information 100, and manufacturer branding information 110. The scroll keys 20, 30 consist of a previous key 20, and a next key 30, while the adjustment keys 50, 60, consist of an up key 50, and a down key 60. For example, the next key 30, enter key 40, up key 50 and down key 60 all have additional functions. The next key 30 can be used to access the Information Center menus, the enter key 40 can be used to access Manual Regeneration menus, the up key can be used to access higher level menus such as the Installer and Service menus, and the down key 60 can be used to access Customer Settings menus. The control unit 10 includes an electronic controller 12, a storage device 14, an input device 16 and a display 18, wherein the electronic controller 12 can be any type of commercially available electronic controller, and the storage device 14 can be RAM, ROM, CD, hard drive, or any commercially available storage device.

The functions and operation of the control unit according to a preferred embodiment of the present invention will now be described with continued reference to FIGS. 1 and 2. The control unit 10 is programmed to prompt the user to enter data relevant to operation, maintenance and repair issues, which then is stored in the storage device 14. If a response to such prompting is not indicated by pressing an appropriate key in a set amount of time, the control unit 10 will timeout, the backlight in the display screen 70 will shut off. When a timeout occurs, the backlight may be re-energized by pressing any key 20, 30, 40, 50, or 60.

At some point prior to installation (e.g., at the point of manufacture and/or distribution), power is supplied to the control unit and a start up routine automatically begins. However, it will be appreciated that a manual start up routine can also be used in the practice of the present invention. A start up message will appear on the display screen 70 to instruct the user to begin the start up routine. The startup message will prompt the user to start an initial electrical test and direct the user to press a key(s) to communicate a response. If the user indicates a desire to start the initial electrical test by pressing the appropriate key(s), the control unit will run the electrical test, ask to run a flow meter test and direct the user to communicate a response by pressing another key(s). If the user indicates a desire to start the flow meter test, the display screen 70 will show the current flow rate screen and will wait a set number of seconds to receive pulses. Once the computer receives pulses it will accept the test as a pass and conclude the electrical test. The start up message is displayed when the control unit is first powered up and will reoccur any time power is turned off and then restored to the control unit until all conditions of the startup routine are met. Once the start up routine conditions are met, the installation routine will begin and the start up message and routine will never be used or displayed again.

In order to begin the installation routine, at least two conditions must be met: 1) the electrical test must have been accessed; and 2) there must be an indication that the electrical system is in working order. Once these conditions have been met, the installation routine will begin. An installation startup message will be displayed and will reoccur any time power is shut off and restored until the installation routine has been completed. The user will be prompted to begin the installation routine and directed to enter specific system installation data manually. The user will enter such requested information by using the scroll 20, 30, enter 40, and adjust 50, 60 keys as necessary. Once all the required data has been entered and saved, the installation routine is complete and the installation routine will no longer be available; however, if the information entered during the installation routine is not saved, the computer will not recognize that the control unit has been installed and the control unit will prompt the user to run the installation routine again the next time power is restored. One preferred embodiment of the present invention includes the following installation functions:

| Installation Information | Example | Explanation |
| --- | --- | --- |
| Units of Measurement | Units: English | This function sets the units of measure of the system between English and Metric. The control unit can covert and recalculate values as necessary to comply with the chosen measurement system. |
| Date/Time | Time of Day: 12:00 AM<br>Current Day: Monday<br>Current Date: Sep. 26, 2005<br>Daylight Savings Time: On | The user will not be allowed to scroll past the current date until it is populated. Once populated the rest of the menu is accessible. The Date/Time information must be entered in order to proceed out of the installation mode to ensure that all treatment system history data will be accurate. |

-continued

| Installation Information | Example | Explanation |
|---|---|---|
| Install Date | Install Date: Jun. 20, 2005 | This function records the date of installation. If power is detected for seven days, the computer will back stamp the date and record the install date in the service history function. This is a one time condition and it cannot be altered. This feature is automatic and can be viewed through the service mode. |
| Control Unit Model | Model: Amazon AQC 100 CV Unit Size: AQC 100 CV Media Type: AQC 100 CV | These functions set the control unit model type, size, and media type. |
| Testing/Analysis | Hardness: 10 Grains Iron: .5 ppm | Tests are performed at the time of installation and the results are entered into the control unit. This data is used to set the treatment systems to the appropriate routines. For example, in the preferred embodiment, the range of water hardness can be set from 1-200, and the iron values are set in .5 ppm increments. |
| System Calculations and Settings | Start Capacity: 30% Total Capacity: 3100 gal Water to Start Regen: 930 gal Salt Level: 6 300 lbs | These functions display various treatment system calculations that are important for efficient operation of those systems. |
| System Alarms | Salt Alarm: On Set for: 5:00 PM Accessory Timers: No "Filter Change . . . For service call: (555) 555-5555" | This function allows the user to set audio and visual alarms for various system conditions. All alarms that require a service call are audible, but can be manually silenced or reset by pressing the appropriate key. Audible alarms can be programmed to sound the audible alarm at any desired hour. Optional alarms for less critical conditions and accessory timers can be programmed to only present a visual alarm or can be switched off altogether. |
| Local Service # | Local Serv. #: (555) 555-5555 | This information is manually entered and is displayed when any alarm is detected. It can be altered by the user when local service providers change. For example, a message banner reporting the alarm would include the following information: "For service call: (555) 555-5555" |
| Save Changes | Save Changes: No | This function exits the user out of the installation routine. If the data is not saved or all the installation information is not completed, the installation routine will re-start or continue the next time the control unit is re-energized. The control unit will prompt the user to save changes in the middle of the list if the user must exit before finishing the installation. This function defaults to "yes" during the start up routine's installation mode. It defaults to "no" when installation mode is manually accessed. |

Once the startup and installation routines are completed, the display screen 70 will revert to a home screen, which displays the control unit's general home screen. From this point on, upon power up/restore, the computer will initialize, turn the backlight on, display a power up message banner, then switch to the home screen and be idle. The home screen is the condition of display when there is no interaction with the control unit or the control unit is in an idle state. The home screen provides the current time and date and will toggle between important treatment system data, such as water conditioner salt levels, and/or graphs indicating remaining water conditioning capacity, among other things. The user is able to view and enter all necessary treatment system information by toggling through the parent menu and its various branch menus by using the scroll keys 20, 30, enter key 40, and adjust keys 50, 60 as necessary.

When the control unit is on but idle any key press will "wake up" the unit by turning on the backlight, displaying a wake up message and then displaying the home screen. Message banners, consisting of a quick message across the screen, can be used at any time, such as at the time of power up or wake up. A message banner can be either static or dynamic depending on the message being displayed. If dynamic, speed of the message scroll is to have minimal choppiness and should be slow enough to allow the user to read the message the first or second time it scrolls across the display screen 70.

A typical power up message will state the control unit product name and/or slogan and then switch to the home screen, while a typical wake up message will display the power up message, display system status information, and then show relevant treatment system condition messages before switching to the home screen. If the message is static and contains more information than the display screen 70 allows, the user will be prompted to use the scroll keys 20, 30 to read the rest of the message.

Customer Settings

Once the control unit is properly installed, the user is able to modify this information and customize various treatment system functions through the Customer Settings menu, which can be accessed by pressing the down key 60. The user can view and enter data here using the scroll keys 20, 30, enter key 40 and adjust keys 50, 60 as desired. The Customer Settings menu of one preferred embodiment of the present invention, includes the following functions:

| Function | Example | Explanation |
| --- | --- | --- |
| Condition Levels | Salt Level: 6 | This function allows the user to manually enter data relating to various treatment system components and conditions that can be found locally at the treatment system itself. |
| Vacation Status | Vacation Mode: Off | This function can be toggled on or off. Vacation mode allows the user to put the treatment systems into hibernation for periods of time. A user can program the system to turn on at a specified time and begin routine operations so that the treatment systems are up and running prior to the users return from an extended absence. |
| Alarms | Salt Alarm: On Set for: 5:00 PM | This function allows the user to set audio and visual alarms for various system conditions. All alarms that require a service call are audible, but can be manually silenced. Audible alarms can be programmed to sound the audible alarm only during waking hours. Optional alarms for less critical conditions can be programmed to only present a visual alarm or can be switched off altogether. |
| Date/Time | Time of Day: 12:00 AM Current Day: Monday Current Date: Sep. 26, 2005 Daylight Savings Time: On | These functions are accessible from multiple menus. They allow the user to program the current date, day, and time. |
| Scheduled Maintenance Operations | Time of Regen: 2:00 AM | These functions allow the user to set a particular time of day that the user desires a regeneration to be performed. |

The control unit allows certain treatment systems operations to be performed automatically and manually. For example, in the case of regeneration for water treatment systems, a user can select manual regeneration from the menu and receive a choice of manual regeneration schemes, allowing the user to regenerate at that time ("Regen Now"), or set a time to regenerate later ("Regen Later"). Regen Later will initiate regeneration at the programmed time, while Regen Now will provide a ten second countdown before initiating the regeneration. The user may cancel a regeneration request at any time prior to its initiation.

Additionally, some less routine treatment system functions may be hidden from certain users (e.g., owners) and made available only to other users (e.g., manufacturers, repair services) to prevent improper use of these functions and to minimize potential damage to the treatment system. For example, in water treatment systems, the control unit can be configured to allow a user to advance through regeneration cycles prior to completion of the previous cycle, or to allow a user to fully advance through the entire regeneration process, bypassing all cycles while in regeneration The control unit may require a combination of key strokes or a certain access code to make these hidden options available so they are only available to users with a need to access those options.

Information Center

The control unit also provides an information center, allowing the user (owner or authorized third party, e.g., installer, manufacturer, maintenance service, repair service) to quickly review the status and usage profile of the associated treatment systems. The information center can be accessed by pressing the next key 30.

The information center reports current alarms and provides general information about the owner's product and water use. A user can use the scroll keys 20, 30 to navigate through the available data menu and choose the desired information to be displayed. The information center will only display information and will not allow changes to be made to the treatment system settings or service data. In one preferred embodiment of the present invention, the information center supplies the following data:

| Information Displayed | Example | Explanation |
| --- | --- | --- |
| Control Unit Model Type | Model Type: AQC 100 CV | Displays the control unit's model type |
| System Status | System Status: Water Conditioner: | Displays the status of each associated treatment system. |

-continued

| Information Displayed | Example | Explanation |
|---|---|---|
| | Low Salt . . . Please Refill . . . Press any key to silence . . . Use Adjust keys to make postpone selection then press enter. Go to Customer Settings to enter salt.<br>Water Filter: OK<br>Drinking Water: OK<br>Air Filter: OK | Where an alarm is detected, the display would indicate the alarm type and provide a related message banner.<br>Alarms may also be set to provide different audio tones to indicate which alarm is detected.<br>When an alarm condition is no longer present (salt has been entered), the system status will return to the "OK" setting and the alarm will no longer sound. |
| Operation Type | Regen Method:<br>Demand Initiate | Displays operation methods currently selected for the treatment system. |
| Condition Levels | Salt Level: 6 | Displays current condition levels. |
| Alarms | Salt Alarm: On<br>Set for: 5:00 PM | Displays alarm on/off settings and alarm set times |
| Scheduled Maintenance Information | Time of Regen: 2:00 AM<br>Est. Next Regen: need more data | Displays information relating to scheduled maintenance operations for various treatment systems. Display will also indicate whether it is able to provide that data. |
| Product Use Information/ System Operation Information | Avg. Water Use:<br>15 gpd<br>Avg. Weekly Salt Used:<br>3 lbs<br>Current Flow Rate:<br>.25 gpm | Displays average consumer use and other useful system information |
| System Test Results/ Analysis | Hardness:<br>10 grain<br>Iron:<br>0 ppm | Displays information gained from water analysis |
| Vacation Status | Vacation Mode:<br>Off | Displays current vacation mode setting.<br>The vacation mode can be programmed to hibernate all treatment systems while the user is out of town and will regenerate the unit one day before the scheduled return date to provide maximum amount of clean treated water, maintain maximum performance and customers satisfaction) |
| Installation Information | Conditioner Installed:<br>Jan. 20, 1998<br>Filter Installed:<br>Apr. 12, 2001<br>Drinking Water Installed:<br>Oct. 03, 2004 | Displays activation date of each treatment system.<br>If the system is not installed or has not yet been activated, this information will not be displayed. |
| Manufacturer/ Service Provider Information | Web Address:<br>www.rainsoft.com<br>Local Serv. #:<br>(555) 555-5555 | Displays manufacturer's corporate web address and local service provider's phone number. |

As noted above, the "system status" portion of the control unit can provide the status of a water conditioner, as well as other units/treatment systems, such as water filters and air filters. In one embodiment of the present invention, the control unit can be programmed with simple timers for such other units/treatment system that sound an alarm for service (such as the replacement of a filter) when a timer expires. However, it is also within the scope of the present invention that such other units/treatment systems can send real-time information to the control unit via any known communication technique (i.e., an, wireless an, cable/wire, ethernet, etc.) thereby providing actual data regarding when service is necessary.

Service Mode

Like the Installation Mode, the Service Mode is a high level menu that can only be accessed by using a special code. The menus available in this mode assist service providers in diagnosing problems with the treatment systems.

| Information Displayed | Example | Explanation |
|---|---|---|
| System Status | System Status:<br>Water Conditioner:<br>Low Salt . . . Please Refill . . . Press any key to silence . . . Use Adjust keys to make postpone selection then press enter. Go to Customer Settings to enter salt.<br>Water Filter: OK<br>Drinking Water: OK | Displays the status of each associated treatment system.<br>Where an alarm is detected, the display would indicate the alarm type and provide a related message banner.<br>Alarms may also be set to provide different audio tones to indicate which alarm is detected.<br>When an alarm condition is no longer |

-continued

| Information Displayed | Example | Explanation |
|---|---|---|
| | Air Filter: OK | present (salt has been entered), the system status will return to the "OK" setting and the alarm will no longer sound. |
| Audio Alarm | Audio Alarm Test: Off | Allows the audio alarm to be manually turned off and on. |
| System Capacities | Total Capacity (water): 3100 gal | Displays the calculated capacities of the various systems based on the installation parameters |
| System Usage/Operation Information | Water to Start Regen: 930 gal<br>Water Available: 930 gal<br>Current Water Used: 0 gal<br>Current Flow Rate: 0 gpm<br>Avg. Water Use: 0 gpd<br>Avg. Weekly Salt Used: 0 lbs<br># Regen 14 Days: 0 regens<br># Regen 28 Days: 0 regens<br>Total Life Regen: 0<br>Total Life Water: 0<br>Show Last Regen Info: No | Displays the calculations and treatment data based on system usage and historical operation.<br>Calculated values will not go below zero.<br>"Total Life" information cannot be reset. |
| System History Information | Display Alarm History? Yes<br>Salt Alarm History<br>Motor Alarm History<br>Power Loss History<br>Display Service History? No | Displays alarm histories that have been detected. Indicates the time and date of all alarms in each sub category of alarms. Service history section displays installation history for the various treatment systems, and repair history for specific coded repair problems and service responses. |
| Revision Numbers | Program Revision: G3 XX 25<br>EEprom Revision: xxxxx | Displays the program revision currently loaded on the computer. |
| Electrical Test | Run Electrical Test? No | This function will perform a self test and report any problems encountered. |
| Override Functions | Primary Motor Override: Off<br>Drive to Cycle: No<br>Drive Primary to Service: No<br>Auxiliary Relay Override: Off<br>Regen Method:<br>Regen Override: Off<br>Backwash Ctrl:<br>Injector Size: | Allows the control unit to manually override the normal system cycles and settings and place the treatment systems into desired cycles for service. |
| Cycle Time Options | Alter Cycle Times? | Allows cycle times to be altered from default settings so they conform with the conditions at hand (e.g., different cycle times required to properly condition hard water vs. soft water). |

As noted above, the system history information portion of the control unit provides the service history for the various treatment systems using codes. It is envisioned that simple character codes, consisting of two or more characters, can be placed into the system by service technicians indicating the nature of the prior problems and how they were fixed. For example, if a regeneration motor on a unit fails, the service technician can enter code "02", which indicates that the motor previously failed and replaced. Accordingly, using such a coded section will allow service technicians to easily identify prior problems and fixes, as well as readily identify recurring problems, which may have other causes. This section can also include codes, such as "NPF" to indicate that no problems were found on the prior service visit, "03" to indicate the need for an injector cleaning, "04" to indicate the need for a seal stack replacement, or "05" to indicate the need for a general valve cleaning.

In another preferred embodiment, the present invention consists of a customized control unit containing pre-programmed installation routines for each of a prescribed number of standard treatment system conditions. Here, the installer would merely have to pick the pre-programmed installation routine that corresponded to the treatment system conditions on site and initiate that routine. The control unit would then be able to automatically enter and save the prescribed installation data, minimizing installation time and potential errors in installation routine data entry.

In yet another preferred embodiment, the present invention would allow for local and remote data extraction and input through use of wireless, cable, "smart card", USB, DSL, bluetooth and similar technologies, ensuring that repair technicians and service providers could easily transport and transmit treatment system data to assist them in providing faster, more comprehensive and cost effective customer service.

The foregoing narrative of various preferred embodiments of the present invention has been presented for purposes of illustration and description, and is not intended to be exhaustive or to limit the invention to the precise form(s) disclosed. The description was selected to best explain the principles of the invention and their practical application to enable others skilled in the art to best utilize the invention in various embodiments and various modifications as are suited to the particular use contemplated. It is intended that the scope of the invention not be limited by the specification, but be defined by the claims set forth below.

What is claimed is:

1. An electronic control unit for at least one water treatment system comprising: a microprocessor; a user interface; a memory; at least one interactive menu; at least one start up routine, wherein said start up routine comprises an electrical test of the microprocessor and non-microprocessor portions of said electronic control unit prior to running at least one installation routine; said installation routine comprises prompting a user for baseline water treatment system information, including water iron content information; and at least one system profile for storing water treatment system information in said memory wherein said system profile is created when said installation routine is completed.

2. The electronic control unit of claim 1, wherein said system profile is updated when maintenance information is entered into said electronic control unit.

3. The electronic control unit of claim 1, wherein said system profile is updated when repair information is entered into said electronic control unit.

4. The electronic control unit of claim 1, wherein said electronic control unit displays system profile information to a user.

5. The electronic control unit of claim 1, wherein said water treatment system information includes system history information.

6. The electronic control unit of claim 1, wherein said system profile information is exchanged between the user and the electronic control unit via data exchange.

7. The electronic control unit of claim 1, wherein said system profile information is exchanged between the user and the electronic control unit via text messaging.

8. The electronic control unit of claim 1, wherein said system profile information is exchanged between the user and the electronic control unit via image messaging.

9. The electronic control unit of claim 1, wherein said system profile information is exchanged between the user and the electronic control unit via phone messaging.

10. The electronic control unit of claim 1, wherein said electronic control unit includes at least one accessory timer.

11. The electronic control unit of claim 1, wherein said baseline water treatment information includes installation date information.

* * * * *